United States Patent
Sealfon et al.

(10) Patent No.: US 11,400,213 B2
(45) Date of Patent: Aug. 2, 2022

(54) PRECISION VARIABLE FLOW RATE INFUSION SYSTEM AND METHOD

(71) Applicant: REPRO-MED SYSTEMS, INC., Chester, NY (US)

(72) Inventors: Andrew I. Sealfon, Monroe, NY (US); Siavash Gheshmi, Chester, NY (US)

(73) Assignee: REPRO-MED SYSTEMS, INC., Chester, NY (US)

( * ) Notice: Subject to any disclaimer, the term of this patent is extended or adjusted under 35 U.S.C. 154(b) by 232 days.

(21) Appl. No.: 16/865,764

(22) Filed: May 4, 2020

(65) Prior Publication Data
US 2020/0261646 A1    Aug. 20, 2020

Related U.S. Application Data

(62) Division of application No. 15/052,727, filed on Feb. 24, 2016, now Pat. No. 10,709,839.
(Continued)

(51) Int. Cl.
*A61M 5/168* (2006.01)
*A61M 5/14* (2006.01)
(Continued)

(52) U.S. Cl.
CPC ........ *A61M 5/16877* (2013.01); *A61M 5/141* (2013.01); *A61M 5/142* (2013.01);
(Continued)

(58) Field of Classification Search
CPC ............. A61M 5/16877; A61M 5/141; A61M 5/1413; A61M 5/142; A61M 5/16813; A61M 5/16886; A61M 5/178
See application file for complete search history.

(56) References Cited

U.S. PATENT DOCUMENTS

| 3,877,428 A | 4/1975 | Seagle et al. |
| 4,904,239 A | 2/1990 | Winchell et al. |

(Continued)

OTHER PUBLICATIONS

PCT International Search Report for International Application PCT/US2016/019600, search report dated Jun. 10, 2016 (Oct. 6, 2016).

*Primary Examiner* — Dung T Ulsh
(74) *Attorney, Agent, or Firm* — Daniel W. Roberts; Law Offices of Daniel W. Roberts, LLC (57) ABSTRACT

Provided is a precision variable flow rate infusion system and method for delivering a liquid from a reservoir having an initial potential outflow rate to a patient. The system includes at least a first flexible flow rate tubing having a pre-defined flow rate selected at a maximum dosage flow rate for the liquid from the reservoir, the pre-defined flow rate being less than the initial potential outflow rate of the reservoir. Also provided is an adjustable flow rate controller having an inlet and an outlet, at least one internal fluid pathway there between and a fluid pathway modifier structured and arranged to modify the internal fluid pathway from the inlet to the outlet from a closed pathway to a maximum flow pathway with a plurality of different flow rate pathways there between. Moreover, the at least first flexible flow rate tubing and adjustable flow rate controller determine the maximum flow rate of liquid from the reservoir to a patient and the adjustable flow rate controller permits precision flow rate control from an off flow rate to about the maximum flow rate permitted. Associated methods of providing, calibrating and using the precision variable flow rate infusion system are also provided.

23 Claims, 7 Drawing Sheets

Related U.S. Application Data

(60) Provisional application No. 62/128,501, filed on Mar. 4, 2015.

(51) Int. Cl.
*A61M 5/142* (2006.01)
*A61M 5/178* (2006.01)

(52) U.S. Cl.
CPC ...... *A61M 5/1413* (2013.01); *A61M 5/16813* (2013.01); *A61M 5/16886* (2013.01); *A61M 5/178* (2013.01)

(56) References Cited

U.S. PATENT DOCUMENTS

| | | |
|---|---|---|
| 5,009,251 A | 4/1991 | Pike et al. |
| 5,234,413 A | 8/1993 | Wonder et al. |
| 5,246,016 A | 9/1993 | Lieber |
| 6,095,491 A | 8/2000 | Kriesel |
| 6,926,706 B1 | 8/2005 | Sealfon |
| 7,955,289 B2 | 6/2011 | O'Mahony et al. |
| 8,070,733 B2 | 12/2011 | Bettini et al. |
| 8,444,592 B2 | 5/2013 | Williams et al. |
| 2002/0115966 A1* | 8/2002 | Christensen ...... A61M 5/16804 604/264 |
| 2003/0097097 A1 | 5/2003 | Scagliarini et al. |
| 2004/0068222 A1 | 4/2004 | Brian |
| 2009/0178459 A1 | 7/2009 | Li |
| 2011/0119464 A1 | 5/2011 | Karr et al. |
| 2013/0138075 A1* | 5/2013 | Lambert ............... A61M 39/10 604/500 |
| 2014/0127209 A1 | 8/2014 | Sealfon |
| 2014/0276198 A1 | 9/2014 | Dunung |

* cited by examiner

PRECISION VARIABLE FLOW RATE INFUSION SYSTEM AND METHOD

CROSS REFERENCE TO RELATED APPLICATIONS

The present application is a Divisional of U.S. patent application Ser. No. 15/052,727, filed Feb. 24, 2016, now U.S. Pat. No. 10,709,839. This Divisional application claims the benefit of U.S. patent application Ser. No. 15/052,727, filed Feb. 24, 2016 and incorporated by reference, which claims the benefit under 35 U.S.C. § 119(e) of U.S. Provisional Application No. 62/128,501 filed Mar. 4, 2015 the disclosure of which is incorporated herein by reference.

FIELD OF THE INVENTION

The present invention relates generally to systems and methods for liquid fluid flow regulation as may be desired for the delivery of liquid for infusion to a patient, and more specifically to systems and methods to safeguard against overdose by regulating adjustable flow rates so they do not exceed a maximum flow rate for a specific infusion fluid.

BACKGROUND

Infusion systems for the delivery of liquid pharmaceuticals are widely used and relied upon by patients and care givers alike. Such delivery is generally made in one of two ways. The first is an immediate delivery from a health care provider or other operator in the form of a simple injection performed with a syringe and a needle directly disposed to the tissue of the patient. For this type of immediate delivery the amount of the pharmaceutical is typically measured by the health care provider or other operator and the rate of delivery is typically based on the speed at which they depress the plunger. Although overmedication can occur, the rate of delivery is rarely an issue with immediate delivery.

The second option is for gradual delivery, wherein a syringe or other reservoir is connected to specific medical tubing for delivery over time. With such time based delivery, overmedication and/or overdose of the pharmaceutical is a very real possibility. Syringes, or other pharmaceutical reservoirs such as fluid bags, are typically easily and commonly adapted for use with many different types of pharmaceutical, however the flow rate for proper delivery of such pharmaceuticals as determined by the manufacturer may very widely. Further, as patient needs and situations are often different, even when dealing with the same type of pharmaceutical it may be desired for different patients to receive flow rates, which again would be at or below the manufacturer's specified maximum delivery rate.

With the ever increasing desire to reduce health care costs, there is a market demand to reduce the costs of providing intravenous and subcutaneous administrations. With infusion over time, one option has been to employ programmable pumps that control the rate of flow, and while effective, such systems can be cost prohibitive for many users. In addition, many programmable pumps are based on the principle of constant flow. Because these systems attempt to maintain the same flow rate regardless of pressure, these systems generally incorporate a warning system to alert the user and/or operator of any dangerous increase in pressure as the pump attempts to maintain that constant flow. If there is an occlusion at the sight of administration, even with an alarm the patient may be injured and/or receive an overdose of the pharmaceutical.

In contrast to constant flow pumps, constant pressure pumps have been found to be safer and are often more financially acceptable to users. As they are generally more simple in construction, they may also lack some of the versatility of programmable flow rate pumps. One option to achieve a specific flow rate is to select tubing with an appropriate pre-set flow rate. Initially appearing to be a low cost option, providing a variety of different flow rate systems, each with a specific flow rate, leads to overhead complexity as well as potentially additional costs. With a large plurality of different systems greater storage and transportation costs and issue exist. Further, some systems may not be used as frequently as others, and confusion when identifying each distinct infusion system may occur. Further still, such specifically set infusion systems by their very nature do not permit the flow rate to change substantially over time, which if there is a desire to increase or decrease the flow rate over the course of administration, or over the course of use, make such single flow rate systems impractical.

Recently, there have been some advancements in flow regulators which strive to provide the user the ability to easily select and modulate the flow rate of a therapeutic agent or pharmaceutical liquid. In general, these flow regulators or flow constriction devices are designed to allow the user or operator to tune a dial and select a flow rate that corresponds to a level of flow constriction within the device.

U.S. Pat. No. 3,877,428 to Seagle, sets forth a Variable Infusion Control Device 10 for selectively controlling the rate of administration of fluids to a patient. The control device provides attachment fittings which allow it to be placed at any point along a supply tube between a reservoir and the patient. As set forth by Seagle, the variability of flow rate is accomplished with concentric capillaries 60 and 62 which may be variably inter connected, the overall length of the resulting combined capillary establishing the flow rate.

U.S. Pat. No. 5,234,413, to Wonder et al, strives to teach a simplified Infusion Rate Regulator Device with fewer elements—with only a gasket 68 disposed within the housing. Here again, Wonder varies the rate of flow not only as a function of the fluid metering groove 30 through which the fluid flows, but also as a function of the cross sectional area of the fluid metering groove 30. Interestingly, Wonder specifically cites to Seagle noting that the Seagle device is manufactured with five parts, raising manufacturing but more importantly resulting in an unacceptably high degree of variance in the tightness of fit between the parts which adversely impacts the consistency of flow rate at any setting.

U.S. Pat. No. 5,009,251 to Pike et al, teaches a flow regulator 22 having an extensive set of internal flow channels which operate as a capillary flow restrictor. Pike states that the length of the flow channel 114, the overall dimension of the control waver 46 and the slowest delivery rate are all interrelated, due to the known relationship of the flow rate through a capillary tube to the capillary tube's cross sectional area and length, which is mathematically described by Poiseuille's Law.

U.S. Pat. No. 6,095,491 to Kriesel, teaches an In-Line Flow Rate Control Device which again is stated as an option to costly and complex flow controllers. More specifically, Kriesel teaches a device 14 having a housing 20 made up of a base portion 22 and a cover portion 23. Disposed within a cavity are two hub portions 42, 46 which provide a fluid tight seal against a rotating knob 50, the rotating knob 50 providing a plurality of different flow restrictors which can be selectively moved into index place with flow passages in the base portion 22 and cover portion 23. These flow restrictors, i.e. orifices, may be microbors 70 of specific sizes, or frits 60 of different porosities.

US Patent Application 2003/0097097 to Scagliarini et al, teaches a Simplified Device for Regulating the Flow Rate of Medical Liquid Directed Towards A Patient. Once again, Scagliarini notes that many flow rate devices have five or more parts and do not actually achieve precise flow regulation. Scagliarini therefore teaches a device 1 having essentially three parts—a first portion 3 to be connected to a first conduit (not shown) of a medical infusion line connected to a reservoir of medical liquid, a second portion 4 to be connected to a second conduit of said line (also not shown) carrying the liquid to the patient, and a gasket 5 disposed between the first portion 3 and the second portion 4. Relative rotation between the first portion 3 and the second portion 4 permits different sized orifices 44, 52 and 66 provided respectively by the first portion 3, the gasket 5 and the second portion 4, to align with concentric recesses provided in second portion 4. By varying the length of flow through the concentric recess the rate of flow may be varied.

US Patent Application 2013/0138075 to Lambert also teaches a Variable Flow Control Device 200 that is provided by an inlet handle 110 providing an inlet port 116, an outlet handle 130 with an outlet port 134 and a seal 120 with orifices 116 enclosed/sandwiched between. Lambert specifically teaches a plurality of different sized orifices that may be selectively aligned between the inlet and the outlet to provide varied flow rate. In addition to specifically referencing Pike and Wonder for complexity, Lambert also discusses issues of alternative flow rate control by stating clearly, that "flow rate control in mechanical, elastomeric and other non-electrical pumps is generally accomplished with the use of certain small diameter tubing (rate set) that regulates the flow. This presents the following limitations: The flow cannot be adjusted during the infusion. Instead a new infusion set has to be used when a different rate is required. This adds cost and it may it may increase the risk of contamination. In order to change the flow rate, the tubing diameter has to change and thus multiple rate sets have to be made available and changed during infusion. This may or may not be possible during certain therapies. The nominal flow rate of these sets does not correspond to the flow rate during use due to the viscosity of the fluid often leading to patient and clinician confusion and errors." Moreover, Lambert is clearly asserting the disclosed flow controller as an alternative to flow rate control based on tubing.

As varied as these and other prior art references are, in all cases an inherent problem may still exist. Each of the above devices appears to provide an option for no flow rate reduction—an open flow option. As such, although each device may permit some degree of flow control, there is a maximum flow rate that may well be dangerous to a patient.

Hence there is a need for a method and system that is capable of overcoming one or more of the above identified challenges.

SUMMARY OF THE INVENTION

Our invention solves the problems of the prior art by providing novel precision variable flow rate infusion system and method.

In particular, and by way of example only, according to one embodiment of the present invention, provided is a precision variable flow rate infusion system for delivering a liquid from a reservoir having an initial potential outflow rate to a patient, including: at least a first flexible flow rate tubing having a pre-defined flow rate selected at a maximum dosage flow rate for the liquid from the reservoir, the pre-defined flow rate being less than the initial potential outflow rate of the reservoir; and an adjustable flow rate controller having an inlet and an outlet, at least one internal fluid pathway there between and a fluid pathway modifier structured and arranged to modify the internal fluid pathway from the inlet to the outlet from a closed pathway to a maximum flow pathway with a plurality of different flow rate pathways there between; wherein the at least first flexible flow rate tubing determines the maximum flow rate of liquid from the reservoir to a patient and the adjustable flow rate controller permitting precision flow rate control from an off flow rate to about the maximum flow rate permitted by the first flexible flow rate tubing.

For yet another embodiment, provided is a precision variable flow rate infusion system for delivering a liquid from a reservoir having an initial potential outflow rate to a patient, including: at least a first flexible flow rate tubing having a pre-defined flow rate; and an adjustable flow rate controller having an inlet and an outlet, at least one internal fluid pathway there between and a fluid pathway modifier structured and arranged to modify the internal fluid pathway from the inlet to the outlet from a closed pathway to a maximum flow pathway with a plurality of different flow rate pathways there between providing from a maximum adjuster flow rate to a zero flow rate; wherein the pre-defined flow rate and the maximum adjuster flow rate cooperatively combining to be equal to or less than a maximum dosage flow rate for the liquid from the reservoir; wherein the combination of the pre-defined flow rate and the maximum adjuster flow rate determine the maximum flow rate of liquid from the reservoir to a patient, and the adjustable flow rate controller permitting precision flow rate control from an off flow rate to about the maximum flow rate permitted by the combination of the pre-defined flow rate and the maximum adjuster flow rate.

In yet another embodiment, provided is a precision variable flow rate infusion system for delivering a liquid from a reservoir having an initial potential outflow rate to a patient, including: an adjustable flow rate controller having an inlet and an outlet, at least one internal fluid pathway there between and a fluid pathway modifier structured and arranged to modify the internal fluid pathway from the inlet to the outlet from a closed pathway to a maximum flow pathway with a plurality of different flow rate pathways there between; a first flexible flow rate tubing having a first pre-defined flow rate, the first flexible flow rate tubing disposed between the reservoir and the inlet of the adjustable flow rate controller; and a second flexible flow rate tubing having a second pre-defined flow rate, the second flexible flow rate tubing disposed between the outlet of the adjustable flow rate controller and the patient; wherein the first pre-defined flow rate and the second pre-defined flow rate and the maximum adjuster flow rate cooperatively combine to be equal to or less than a maximum dosage flow rate for the liquid from the reservoir; and wherein the combination of first pre-defined flow rate and the second pre-defined flow rate and the maximum adjuster flow rate determine the maximum flow rate of liquid from the reservoir to a patient, and the adjustable flow rate controller permitting precision flow rate control from an off flow rate to about the maximum flow rate permitted by the combination of the first pre-defined flow rate, the second pre-defined flow rate and the maximum adjuster flow rate.

For another embodiment, provided is a method for providing a precision variable flow rate infusion system for delivering a liquid from a reservoir having an initial potential outflow rate to a patient at a flow rate equal to or less than a maximum dosage flow rate for the liquid, including: providing an adjustable flow rate controller having an inlet and an outlet, at least one internal fluid pathway there between and a fluid pathway modifier structured and arranged to modify the internal fluid pathway from the inlet to the outlet from a closed pathway to a maximum flow pathway with a plurality of different flow rate pathways there between; providing a first flexible flow rate tubing having a first pre-defined flow rate, the first flexible flow rate tubing disposed between the reservoir and the inlet of the adjustable flow rate controller; and providing a second flexible flow rate tubing having a second pre-defined flow rate, the second flexible flow rate tubing disposed between the outlet of the adjustable flow rate controller and the patient; wherein the first pre-defined flow rate and the second pre-defined flow rate and the maximum adjuster flow rate cooperatively combine to be equal to or less than a maximum dosage flow rate for the liquid from the reservoir; and wherein the combination of first pre-defined flow rate and the second pre-defined flow rate and the maximum adjuster flow rate determine the maximum flow rate of liquid from the reservoir to a patient, and the adjustable flow rate controller permitting precision flow rate control from an off flow rate to about the maximum flow rate permitted by the combination of the first pre-defined flow rate, the second pre-defined flow rate and the maximum adjuster flow rate.

DETAILED DESCRIPTION

Before proceeding with the detailed description, it is to be appreciated that the present teaching is by way of example only, not by limitation. The concepts herein are not limited to use or application with a specific system or method for providing a certificate, and more specifically a certificate for network access. Thus although the instrumentalities described herein are for the convenience of explanation shown and described with respect to exemplary embodiments, it will be understood and appreciated that the principles herein may be applied equally in other types of precision variable flow rate infusion systems and methods.

This invention is described with respect to preferred embodiments in the following description with reference to the Figures, in which like numbers represent the same or similar elements. Further, with the respect to the numbering of the same or similar elements, it will be appreciated that the leading values identify the Figure in which the element is first identified and described, e.g., element 100 appears in FIG. 1.

Figure 1:
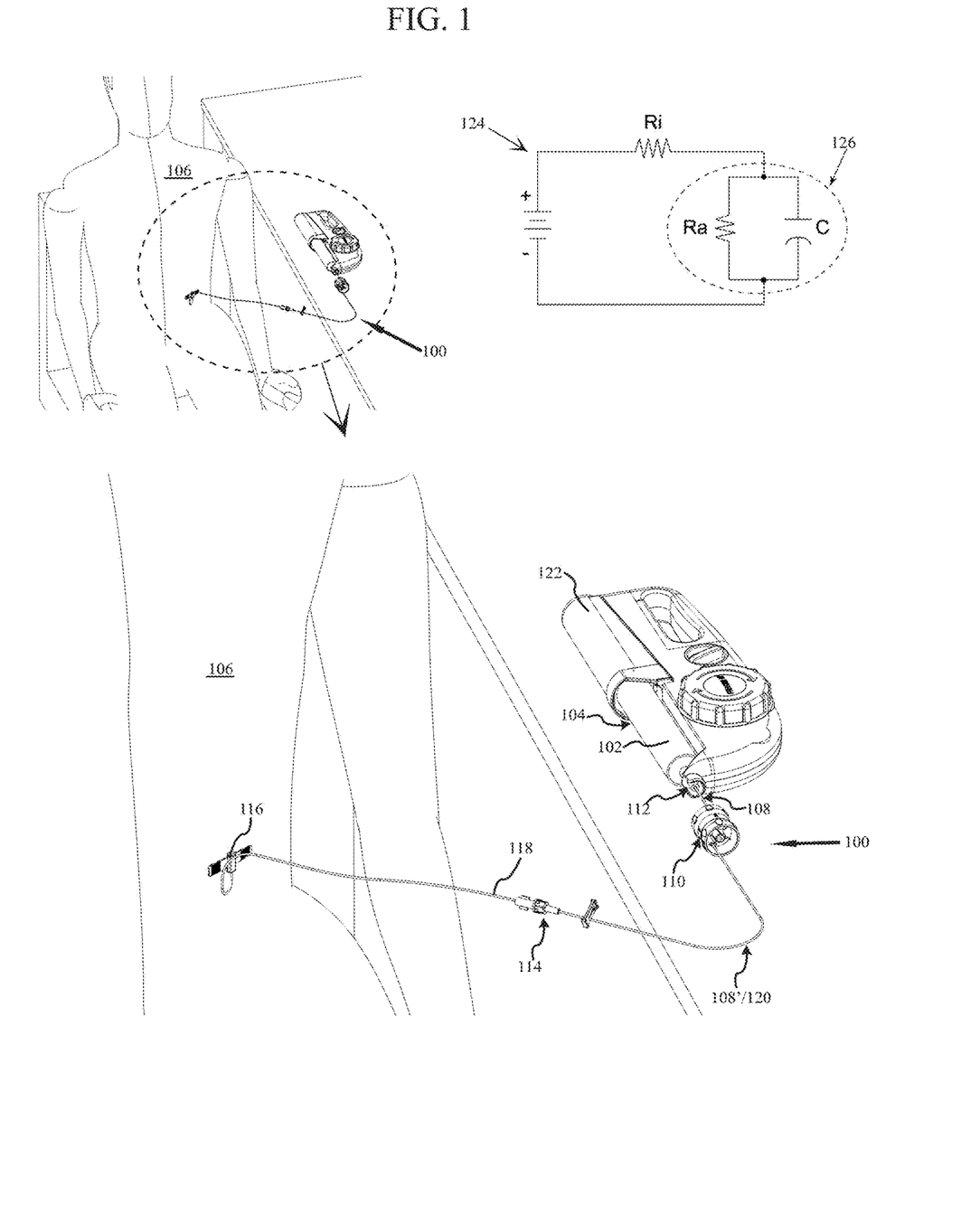
FIG. 1 is a general illustration of a precision variable flow rate infusion system in accordance with at least one embodiment.

Turning now to the drawings, and more specifically FIG. 1, there is shown a precision variable flow rate infusion system 100, hereinafter PVFRIS 100, according to at least one embodiment. PVFRIS 100 is understood and appreciated as an advantageous infusion system for delivering a liquid 102 from a reservoir 104 having an initial potential outflow rate to a patient 106.

As shown, PVFRIS 100 is generally provided by at least a first flexible flow rate tubing 108 having a pre-defined flow rate selected to be at a maximum dosage flow rate for the liquid 102 from the reservoir 104, and an adjustable flow rate controller 110. Moreover, the term "flexible" as applied to flow rate tubing 108 is understood and appreciated to mean that the flow rate tubing 108 is relatively pliable and will easily conform by bending and twisting by an operator. Further, flexible flow rate tubing 108 may also be referred to as flow control tubing, or flow rate control tubing.

It is specifically understood and appreciated that first flexible flow rate tubing 108 is not general medical tubing. Although a tube by it's very nature of being a tube may impart some element of flow restriction based on the size and length of the tube, general medical tubing has such a substantial inside diameter that any contribution of flow rate reduction is effectively negligible when dealing with liquids having a maximum dosage flow rate. In contrast, first flexible flow rate tubing 108 has been specifically manufactured to have a specific length and inside diameter so as to achieve a very specific and pre-defined flow rate.

Flexible flow rate tubing 108 is specifically developed to provide a laminar flow, also known as a streamline flow. Laminar flow occurs when a fluid flows in parallel layers, with no disruption between the layers. At low velocities, the fluid tends to flow without lateral mixing, which means that the adjacent layers slide past one another. This lack of mixing between layers means that there are no cross-currents, eddies or swirls of the fluid—the motion of the particles of the fluid is very ordinary with all particles moving in a straight line relative to the side walls of the flexible flow rate tubing 108.

With respect to fluid dynamics, the Reynolds number is an important parameter in equations that describe whether fully developed flow conditions lead to laminar or turbulent flow. The Reynolds number is the ratio of the internal force to the shearing force of the fluid—in other words, how fast the fluid is moving relative to how viscous the fluid is, irrespective of the scale of the fluid system. Laminar flow generally occurs when the fluid is moving slowly or the fluid is very viscous.

The specific calculation of the Reynolds number and the values where laminar flow occurs depends on the geometry of the flow system and flow pattern, in this case primarily the flexible flow rate tubing 108, which parallels the common example of flow through a pipe, where the Reynolds number is defined as:

$$Re = \frac{\rho v D_H}{\mu} = \frac{v D_H}{v} = \frac{Q D_H}{vA}$$

where:

$D_H$ is the hydraulic diameter of the pipe (flow rate tubing 108); its characteristic travelled length, L, (m).

Q is the volumetric flow rate (m³/s).

A is the pipe cross-sectional area (m²) of the pipe (flow rate tubing 108).

V is the mean velocity of the fluid (SI units: m/s).

$\mu$ is the dynamic viscosity of the fluid (Pa·s=N·s/m²=kg/(m·s)).

V is the kinematic viscosity of the fluid (V=$\mu/\rho$) (m²/s).

$\rho$ is the density of the fluid (kg/m³).

Moreover, flexible flow rate tubing 108 is designed with specific characteristics in light of the above Reynolds equation so as to provide an environment conducive to Laminar flow of intended fluids for use with PVFRIS 100.

Although a low flow rate may be directed through general medical tubing, the low flow rate is achieved by means other than the general tubing, as general tubing does not impart a significant element of flow rate control. When and as the flow rate increase through the general medial tubing, more often then not the flow rate becomes transient, also known as unsteady, or even turbulent. In either case, the flow rate is not consistent and may be problematic.

With respect to PVFRIS 100, by being structured and arranged to provide a laminar flow, flexible flow rate tubing 108 is able to impart and maintain a very consistent pre-determined flow rate, which as is further described below, is highly advantageous to PVFRIS 100. With respect to PVFRIS 100 and more specifically flexible flow rate tubing 108, laminar flow is defined as fluid flow with Reynolds numbers less than 2300.

More specifically, for at least one embodiment the pre-determined flow rate of the first flexible flow rate tubing 108 is selected from the group consisting of: about 30 mL/hr, about 45 mL/hr, about 60 mL/hr, about 120 mL/hr, about 180 mL/hr, about 420 mL/hr, about 600 mL/hr, about 900 mL/hr, about 1200 mL/hr, and about 2400 mL/hr.

The nature of the flexible flow rate tubing 108 to advantageously provide laminar flow, is further enhanced in situations where the liquid being infused to the patient 106 is a Newtonian fluid. A Newtonian fluid is a fluid in which the viscous stresses arising from its flow are linearly proportional to the local strain rate, which is the rate of change of deformation over time. Pure water is not generally a Newtonian fluid, however pure water by itself is not generally the fluid provided by an infusion system. As infusion treatments generally are intended to provide the patient with a specific medication or composition, many of the fluids desired for use with PVFRIS 100 are Newtonian fluids. As such, the ability of PVFRIS 100 to provide fine grain flow control is further enhanced.

It should be understood from the outset that for PVFRIS 100, the flexile flow rate tubing 108 establishes the maximum fluid flow rate for PVFRIS 100. In general the adjustable flow rate controller 110 is inseparably joined with flexible flow rate tubing 108 such that PVFRIS 100 cannot be easily disassembled. This is to ensure that the possibility of accidental flow rate overdose is as minimized as possible. It will be understood and appreciated that PVFRIS 100 has an inlet 112 for connection to the reservoir 104 providing the liquid 102 and an outlet 114 typically connected to a needle 116 or needle system 118 that has at least partially been disposed in the patient 106. Needle 116, and or needle system 118 are typically intended to be disposable after an infusion treatment, the outlet 114 thus permitting disconnection from the disposable element while permitting PFRIS 100 to be reused. In addition, the tubing of needle system 118 is typically general medical tubing, and therefore does not significantly alter the flow rate as established by PFRIS 100.

There are therefore three general configurations for PVFRIS 100 as comprised of flexible flow rate tubing 108 and the adjustable flow rate controller 110.

I. A first configuration is for the flexible flow rate tubing 108 to extend from the inlet 112 coupled to the reservoir 104 to the adjustable flow rate controller 110, and the adjustable flow rate controller provides the outlet 114 coupled to the needle 116 (Flow Tubing 108 to Controller 110).

II. A second configuration is for the adjustable flow rate controller 110 to be spliced into the flexible flow rate tubing 108, such that a portion exists on either side, one tubing end connected to the inlet 112 coupled to the reservoir 104 and the other tubing end coupled to the outlet 114 coupled to the needle 116 (first section Flow Rate Tubing 108, to Controller 110, to second section Flow Rate Tubing 108').

III. A third configuration is for the adjustable flow rate controller 110 to be directly coupled to, or provide, the inlet 112 which in turn is coupled to the reservoir 104 with the flexible flow rate tubing 108 extending from the adjustable flow rate controller 110 to the outlet 114 coupled to the needle 116 (Controller 110 to Flow Rate Tubing 108).

Although each of these general configurations may be preferred for various different embodiments of PVFRIS 100, splicing the adjustable flow rate controller 110 between two sections of flexible flow rate tubing 108 may provide certain advantages, such as, but not limited to, easier access and operation of the adjustable flow rate controller 110. As such, the second configuration will be the primary focus for the remainder of this discussion, though it is understood and appreciated that the elements herein described are likely directly applicable to the first configuration and/or the third configuration as well.

As the second configuration involves splicing the adjustable flow rate controller 110 between two parts of adjustable flow rate tubing 108 and 108', each inseparably joined to the adjustable flow rate controller 110, for at least one embodiment it may be helpful to further view an embodiment of PVFRIS 100 having a first flexile flow rate tubing 108 and a second flexible flow rate tubing 120, the first flexible flow rate tubing 108 disposed between the inlet 112 and the adjustable flow rate controller 110 and the second flexible flow rate tubing 120 being disposed between the adjustable flow rate controller 110 and the outlet 114.

More specifically, the first flexible flow rate tubing 108 and the second flexible flow rate tubing 120 may be two parts of an original single element of flexible flow rate tubing 108, or substantially the same flexible flow rate tubing having about the same flow rate properties. For at least one alternative embodiment, the first flexible flow rate tubing 108 and the second flexible flow rate tubing 120 may be different with the flow rate of one being greater then the flow rate of the other.

For this second configuration utilizing the first flexible flow rate tubing 108 having a first pre-determined flow rate and the second flexible flow rate tubing 120 having a second pre-determined flow rate, the first pre-defined flow rate and the second pre-defined flow rate cooperatively combine to be equal to or less than a maximum dosage flow rate for the liquid 102 from the reservoir 104. In addition, for at least one embodiment, the first pre-defined flow rate and the second pre-defined flow rate are each less than the initial potential outflow rate of the reservoir 104.

And again, for at least one embodiment of the present invention of PVFRIS 100, both the first flexible flow rate tubing 108 and the second flexible flow rate tubing 120 are structured and arranged to provide laminar flow for intended infusion liquid 102.

For at least one embodiment the pre-determined flow rate of the first flexible flow rate tubing 108 is selected from the group consisting of: about 30 mL/hr, about 45 mL/hr, about 60 mL/hr, about 120 mL/hr, about 180 mL/hr, about 420 mL/hr, about 600 mL/hr, about 900 mL/hr, about 1200 mL/hr, and about 2400 mL/hr. Similarly, for at least one embodiment the pre-determined flow rate of the second flexible flow rate tubing 120 is selected from the group consisting of: about 30 mL/hr, about 45 mL/hr, about 60 mL/hr, about 120 mL/hr, about 180 mL/hr, about 420 mL/hr, about 600 mL/hr, about 900 mL/hr, about 1200 mL/hr, and about 2400 mL/hr.

For at least one embodiment, PVFRIS 100 is intended for use with a constant pressure pump 122, such as the Freedom60® Syringe Infusion Pump as provided by RMS Medical Products of Chester, N.Y. Constant pressure systems, such as constant pressure pump 122, when combined with PVFRIS 100 may be highly advantageous in preventing unintended and/or unsafe rates of administration of the liquid 102 to the patient 106.

With a constant flow rate system, the pressure is increased in response to any flow restriction no matter if such a restriction is the build up of pressure in the patient's tissues or an element of the delivery system. This can result in an administration of the liquid at a unsafe pressure. As such, the patient may suffer a wide range of symptoms, including, but not limited to, vein collapse, anaphylaxis, overdose, histamine reactions, morbidity, and mortality.

In sharp contrast, with a constant pressure rate system, such as constant pressure pump 122, if there is a pinch in the tubing, blockage in the infusion system or blockage in the patient's body (such as by saturation of the tissues), results in resistance to the flow and affects the flow rate, not the pressure, i.e., the flow rate decreases as the pressure increases. A constant pressure system may be compared to a theoretical model of an electrical system 124 shown in FIG. 1.

For electrical system 124, as resistance increases 126, the current will immediately and proportionally decrease. A constant pressure infusion system produces this same result: if the resistance to flow increases, the system will immediately adjust by lowering the flow rate. This insures—by design—that a patient 106 can never be exposed to a critically high pressure of liquid 102.

Moreover, as PVFRIS 100 establishes an upper boundary for flow rate of a liquid 102 from a reservoir 104 at or below a pre-defined flow rate, embodiments of PVFRIS 100 are suitable for infusion treatments with constant pressure systems. Additional advantages may be provided when embodiments of PVFRIS 100 are combined with constant pressure pump 122 such as the Freedom60®.

Figure 2:
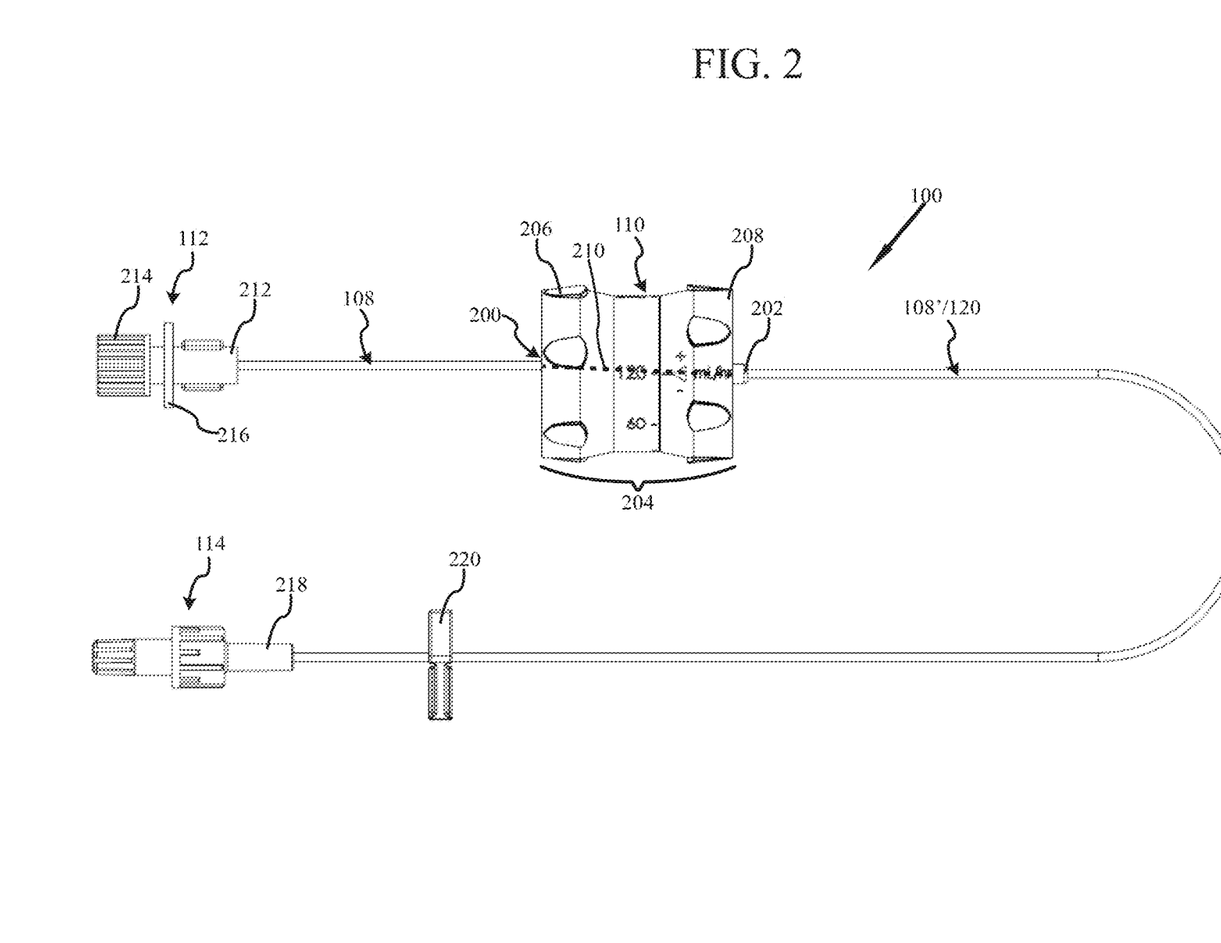
FIG. 2 illustrates an enlarged plane view of a precision variable flow rate infusion system in accordance with at least one embodiment.
Figure 3:
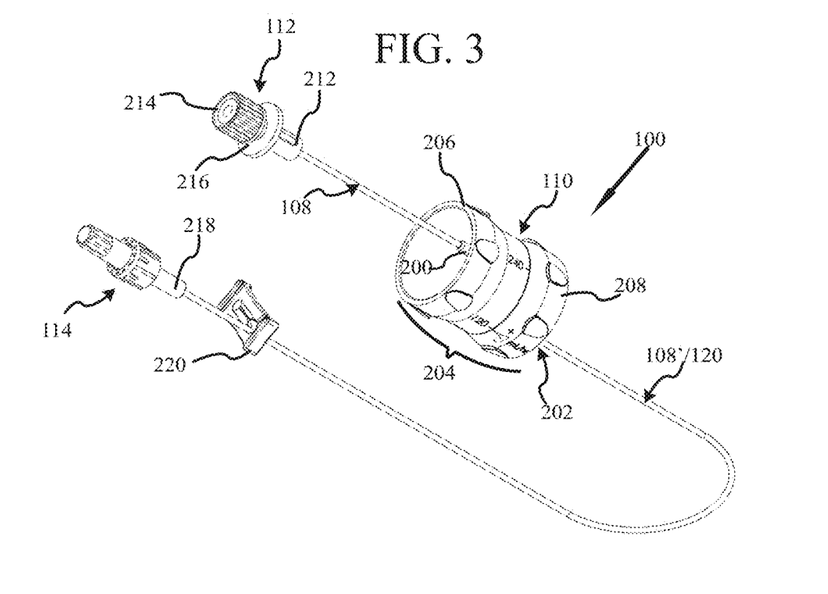
FIG. 3 is a perspective view of the precision variable flow rate infusion system as shown in FIG. 2 in accordance with at least one embodiment.
Figure 4:
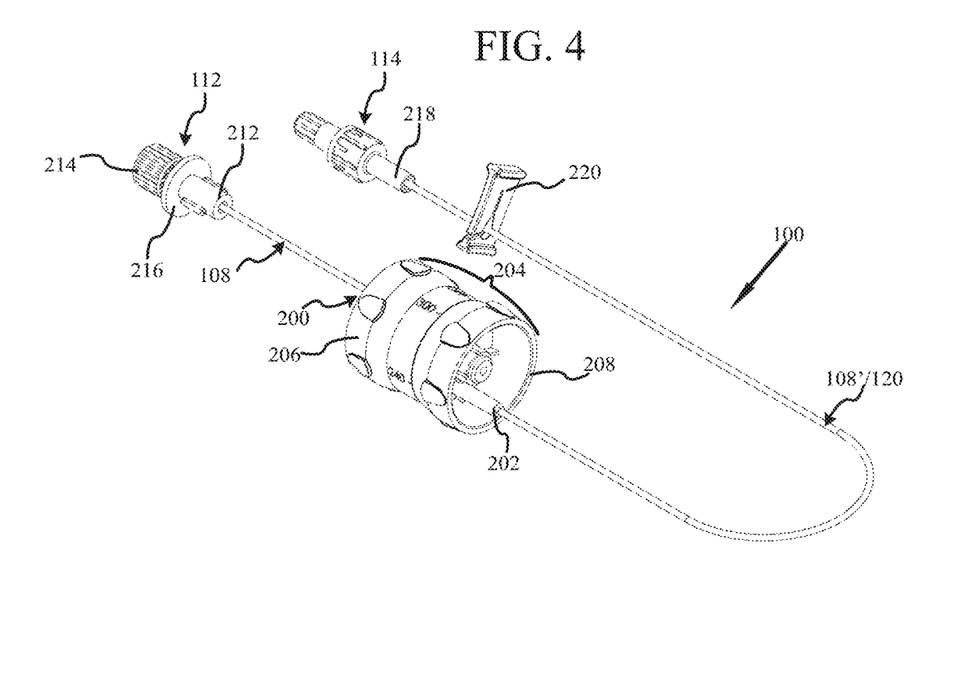
FIG. 4 is an alternative perspective view of the precision variable flow rate infusion system as shown in FIG. 2 in accordance with at least one embodiment.

FIGS. 2-4 provide enlarged conceptual illustrations of PVFRIS 100. More specifically, FIG. 2 is a top plain view of PVFRIS 100 and FIGS. 3 and 4 are alternating perspective views of PVFRIS 100, each further illustrating at least one embodiment of an exemplary flow rate controller 110 for ease of discussion and illustration, and not by way of limitation.

As shown in FIG. 2, the adjustable flow rate controller 110 has an inlet 200 and an outlet 202. Disposed between the inlet 200 and the outlet 202 is at least one fluid pathway within the adjustable flow rate controller 110. Indeed the essence of the adjustable flow rate controller 110 is the ability to adjust the nature of the at least one fluid pathway to provide in a first instance, an unrestricted fluid pathway imparting no significant fluid flow restriction between the inlet 200 and the outlet 202, and to provide in a second instance a complete obstruction of the fluid pathway so as to cease all fluid flow between the inlet 200 and the outlet 202, and in a third instance to provide a user selected degree of flow restriction between the between the inlet 200 and the outlet 202.

Moreover, for at least one embodiment, the adjustable flow rate controller 110 has a maximum adjuster flow rate that is effectively an unrestricted flow rate—the maximum fluid flow rate being for PVFRIS 100 being determined by the combination of the first pre-determined flow rate of the first flexible flow rate tubing 108 and the second-predetermined flow rate of the second flexible flow rate tubing 118. In other words, for at least one embodiment, when the adjustable flow rate controller 110 is set for the maximum adjuster flow rate, it is as if the adjustable flow rate controller 110 was not present.

For at least one alternative embodiment, the adjustable flow rate controller 110 may have a maximum adjuster flow rate that is restricted such that the maximum flow is not an unrestricted flow rate. For such an embodiment, it is to be understood and appreciated that the maximum flow rate for PVFRIS 100 is therefore the cooperative combination of the maximum adjuster flow rate, the first pre-determined flow rate of the first flexible flow rate tubing 108 and the second-predetermined flow rate of the second flexible flow rate tubing 118, this combined maximum flow rate predetermined to be equal to or less than the maximum dosage flow rate for the liquid 102 from the reservoir 104.

The adjustable flow rate controller 110 may be provided in a variety of forms so as to achieve variable flow rate control. Moreover, the adjustable flow rate controller 110 is understood and appreciated to have an inlet 200 and an outlet 202 with at least one internal fluid pathway there between and a fluid pathway modifier 204 structured and arranged to modify the internal fluid pathway from the inlet to the outlet from a closed pathway to a maximum flow pathway with a plurality of different flow rate pathways there between.

This exemplary flow rate controller 110 is shown to have a first end 206 and a second end 208. The first end 206 is providing the inlet 200 (see FIG. 3 showing inlet 200 clearly) and the second end 208 is providing the outlet 208. Within the adjustable flow rate controller 110 is at least one internal fluid pathway, conceptualized by dotted line 210, generally connecting the inlet 200 of the first end 206 with the outlet 202 of the second end 208.

For this exemplary flow rate controller 110, the inlet 200 and the outlet 202 are rotatable about the longitudinal axis of the adjustable flow rate controller 110 relative to each other, which is to say that the first end 206 is rotatable relative to the second end 208. This relative rotation of the inlet 200 to the outlet 202 alters the internal pathway from a closed pathway to a maximum flow pathway with a plurality of different flow rates there between.

For at least one embodiment, the relative rotation of the inlet 200 and the outlet 202 is the fluid pathway modifier 204 as it changes the configuration of at least one fluid pathway within the adjustable flow rate controller 110 between the inlet 200 and the outlet 202, such as by making the internal pathway longer or shorter. Moreover, for at least one embodiment the adjustable flow rate controller 110 provides an internal channel having a length and at least one characteristic that is varied along the length, the length of the channel as between the inlet 200 and the outlet 202 varying as the inlet 200 and the outlet 202 are rotated relative to each other.

For at least one alternative embodiment, the relative rotation of the inlet 200 and the outlet 202 selects one or more alternative fluid pathways within the adjustable flow rate controller 110 between the inlet 200 and the outlet 202, such as by selecting or deselecting one or more fluid channels, each having a different flow rate, to provide a range of variable flow rates. Moreover, the adjustable flow rate controller 110 provides the plurality of different flow rate pathways by disposing differently sized orifices between the inlet 200 and the outlet 202.

Moreover, it is understood and appreciated that the adjustable flow rate controller 110 advantageously permits PVFRIS 100 to provide a variably selected flow rate that is equal to or less than the maximum dosage flow rate for the liquid 102 from the reservoir 104. It should be further understood and appreciated that for at least one embodiment, this variability of flow rate may be user adjustable such that the end patient may adjust his or her flow rate of the liquid 102 during a treatment or from one treatment to the next.

For yet another embodiment, it should be understood and appreciated that the variable selected flow rate may be selected and fixed by an operator such as a doctor, pharmacist or technician, prior to PVFRIS 100 being provided to the end patient. In varying embodiments the variable selected flow rate may be fixed by a collar, pin, glue, or such other device or material that is sufficient to lock the adjustable flow rate controller 110 in a selected position.

Such an ability to permanently fix the selected flow rate advantageously permits a general plurality of PVFRIS 100 to be kept on hand, or in inventory, yet still permit a very precise flow rate setting to be prescribed for the end patient, based on his or her treatment and/or a variety of different liquids 102 that may be provided for infusion by PVFRIS 100. Moreover, PVFRIS 100 advantageously reduces excess inventory and potentially reduces inadvertent error by errantly selecting the wrong preconfigured fixed flow rate system for a particular end patient or infusion liquid 102.

For at least one embodiment the adjustable flow rate controller 110 is an off the shelf component such as the adjustable flow rate controller shown and described in U.S. Pat. No. 8,070,733 to Bettini et al., incorporated herein by reference. For at least one alternative embodiment, the adjustable flow rate controller 110 is an off the shelf component such as the adjustable flow rate controller shown and described in U.S. Pat. No. 5,234,413 to Wonder et al., incorporated herein by reference. For still yet another alternative embodiment, the adjustable flow rate controller 110 is an off the shelf component such as the adjustable flow rate controller shown and described in U.S. Pat. No. 6,926,706 to Sealfon, incorporated herein by reference.

U.S. Pat. No. 6,926,706 to Sealfon teaches a novel variable flow rate controller wherein four internal capillaries are connected in a binary fashion to permit fifteen different flow rates in one assembly. More specifically, the rotation of a knob, i.e., the pathway modifier 204, directs different bosses to be disposed against each of four pistons operating valves which in turn open or close each of the four capillaries.

As is also shown in FIGS. 2-4, in varying embodiments of PVFRIS 100 the inlet 112 may be a luer 212 such as a female luer. Further still, luer 212 may be specifically structured and arranged such that it can only mate with reservoir 104, or rather a specific instance of reservoir having a liquid 102 therein with a maximum directed flow rate, the flow rate of flow rate tubing 108 having been therefore selected to prevent flow rate overdose.

Inlet 112 may also have a removable protective cap 214 serving to protect the inlet 112 from contamination prior to use. For at least one embodiment, the luer 212 of inlet 112 may optionally further include a disk 216 or flared member which is structured and arranged to elevate the inlet 112 away from surface contaminants in the event that the inlet 112 is set down with the protective cap 214 removed. In addition, the optional disc 216 or flared member may be additionally structured and arranged to be received by a specific pump system, such as, but not limited to the Freedom60® Syringe Infusion Pump. For such embodiments, it is further understood and appreciated that the luer 212 is structured and arranged to receive the tip of a syringe, the syringe being the reservoir 104 providing liquid 102.

Moreover, inlet 112 as a flared member is achieved in accordance with the systems and methods as set forth in U.S. Patent Application 62/274,487 and non-provisional U.S. patent application Ser. No. 15/291,895, now U.S. Pat. No. 10,500,389 claiming priority thereto, each entitled "SYSTEM AND METHOD FOR FLARED LUER CONNECTOR FOR MEDICAL TUBING" and each incorporated herein by reference.

Similarly, the outlet 114 may be a luer 218, such as a male luer. Further still, luer 218 may be specifically structured and arranged such that it cannot mate with reservoir 104. Rather luer 218 of the outlet 114 may be structured and arranged such that it may only be connected to a specific needle or specific needle set.

As is also shown, for at least one embodiment, second flexible flow rate tubing 120 may optionally have a slide clamp 220, such as a movable slide camp, that may be used to pinch the second flexible flow rate tubing 120 and stop the flow of liquid 102 through second flexible flow rate tubing 120 regardless of what setting may or may not be selected on the adjustable flow rate controller 110.

Further still, inlet 112 may have a filter element (not shown) which is provided to filter containments from the liquid before entering the flow rate tubing 108 or adjustable flow rate controller 110.

Further still, outlet 114 may optionally also provide a removable protective cap, not shown. For at least one embodiment, the outlet 114, and more specifically luer 218, is inseparably bonded to a needle or needle set. It is to be understood and appreciated that the needle or needle set used with PVFRIS 100 can be of different lengths and different gauges (different diameters, inner and outer). If a plurality of needles are used, i.e., an output set, the multiple needles can be the same or different, such as needles with different lengths for varying areas of the body. In some embodiments, the one or more needles can be selected from 24-gauge needles or narrower such as 25-gauge or 26-gauge needles. In some embodiments, three 9-10 mm needles can be used in the outlet for subjects receiving up to 75 mL of a therapy such as Hizentra®. In some embodiments, a range of needles or needle sets can be used with the flow controller system, including lower gauge (larger diameter) needles for faster administration as compared to higher gauge (narrower) needles because the first flexible flow rate tubing 108, and or the second flexible flow rate tubing 120, and or adjustable flow rate controller 110 again limit the liquid 102 flow rate of PVFRIS 100 to a safe defined maximal output flow rate.

As noted above, for at least one embodiment, the components of PVFRIS 100 are inseparably bonded. Moreover first flexible flow rate tubing 108, and or the second flexible flow rate tubing 120 may be joined to the inlet 200 and outlet 202 of the adjustable flow rate controller 110 by sonic welding or with UV adhesive, such as but not limited to DYMAX® 1120-M-UR UV Glue, DYMAX® 1120-M-T-UR UV Glue. Likewise, by sonic welding or UV adhesives may be used for the bonding of luer 212 to inlet 112 or luer 218 to outlet 114.

Moreover, for at least one embodiment PVFRIS 100 may be summarized as having at least a first flexible flow rate tubing 108 having a pre-defined flow rate selected at a maximum dosage flow rate for the liquid 102 from the reservoir 104, the pre-defined flow rate being less than the initial potential outflow rate of the reservoir 104; and an adjustable flow rate controller 110 having an inlet 200 and an outlet 202, at least one internal fluid pathway there between and a fluid pathway modifier 204 structured and arranged to modify the internal fluid pathway from the inlet 200 to the outlet 202 from a closed pathway to a maximum flow pathway with a plurality of different flow rate pathways there between; wherein the at least first flexible flow rate tubing 108 determines the maximum flow rate of liquid 102 from the reservoir 104 to a patient 106 and the adjustable flow rate controller 110 permitting precision flow rate control from an off flow rate to about the maximum flow rate permitted by the first flexible flow rate tubing 108.

For at least one alternative embodiment of PVFRIS 100 may be summarized described as having at least a first flexible flow rate tubing 108 having a pre-defined flow rate; and an adjustable flow rate controller 110 having an inlet 200 and an outlet 202 with, at least one internal fluid pathway there between and a fluid pathway modifier 204 structured and arranged to modify the internal fluid pathway from the inlet 200 to the outlet 202 from a closed pathway to a maximum flow pathway with a plurality of different flow rate pathways there between providing from a maximum adjuster flow rate to a zero flow rate; wherein the pre-defined flow rate and the maximum adjuster flow rate cooperatively combining to be equal to or less than a maximum dosage flow rate for the liquid 102 from the reservoir 104; wherein the combination of the pre-defined flow rate and the maximum adjuster flow rate determine the maximum flow rate of liquid 102 from the reservoir 104 to a patient 106, and the adjustable flow rate controller 110 permitting precision flow rate control from an off flow rate to about the maximum flow rate permitted by the combination of the pre-defined flow rate of the first flexible flow rate tubing 108 and the maximum adjuster flow rate of the adjustable flow rate controller 110

For yet at least one alternative embodiment, PVFRIS 100 may be summarized as having an adjustable flow rate controller having an inlet 200 and an outlet 202 with at least one internal fluid pathway there between and a fluid pathway modifier 204 structured and arranged to modify the internal fluid pathway from the inlet 200 to the outlet 202 from a closed pathway to a maximum flow pathway with a plurality of different flow rate pathways there between providing from a maximum adjuster flow rate to a zero flow rate. PVFRIS 100 further includes a first flexible flow rate tubing 108 having a first pre-defined flow rate, the first flexible flow rate tubing 108 disposed between the reservoir 104 and the inlet 112 of the adjustable flow rate controller 110. PVFRIS 100 also includes a second flexible flow rate tubing 120 having a second pre-defined flow rate, the second flexible flow rate tubing 120 disposed between the outlet 200 of the adjustable flow rate controller 110 and the patient 106. And again, the first and second pre-defined flow rates of the first and second flexible flow rate tubing 108, 120 and maximum adjuster flow rate of the adjustable flow rate controller 110 combine to be equal to or less than a maximum dosage flow rate for the liquid 102 from the reservoir 104. Further, the combination of first pre-defined flow rate and the second pre-defined flow rate and the maximum adjuster flow rate determine the maximum flow rate of liquid 102 from the reservoir 104 to a patient 106, and the adjustable flow rate controller 110 permitting precision flow rate control from an off flow rate to about the maximum flow rate permitted by the combination of the first pre-defined flow rate, the second pre-defined flow rate and the maximum adjuster flow rate.

Moreover, in sharp contrast to the traditional practice of incorporating an adjustable flow rate controller with typical medical tubing, in PVFRIS 100 the first flexible flow rate tubing 108 and adjustable flow rate controller 110 determines the maximum flow rate of liquid 102 from the reservoir 104 to the patient 106 and the adjustable flow rate controller 110 permits precision flow rate control from an off flow rate to an about the maximum flow rate permitted by the first flexible flow rate tubing 108.

It should also be understood and appreciated, that unlike a traditional infusion system using general medical tubing with a flow adjustment controller, wherein the flow rate is truly and entirely dependent upon the flow adjustment controller, in PVFRIS 100 both the flow rate tubing 108 and the adjustable flow rate controller 110 both must be appreciated for their respective roll in overall flow rate control.

More specifically, as noted above, first flexible flow rate tubing 108 and second flexible flow rate tubing 120 are both structured and arranged to provide laminar flow. In addition, as noted above, a large percentage of the liquids 102 intended for use with PVFRIS 100 are Newtonian fluids. Although in some applications the infusion fluid may not be a Newtonian fluid, a brief discussion of laminar flow and Newtonian fluids with respect to PVFRIS 100 may helpful in further appreciating the advantages of PVFRIS 100.

For a Newtonian fluid, having a flow rate of X thorough first flow rate tubing 108, adding a second flow rate tubing 120 with substantially the same flow rate properties does not provide an overall flow rate of X, rather it is ($\frac{1}{2} \times X$). Adding a third flow control tubing with substantially the same flow rate properties provides an overall flow rate of ($\frac{1}{3} \times X$). As the adjustable flow rate controller 110 provides optional settings optimally from no restriction to full restriction, the restriction of flow rate imparted by the flow rate controller 110 to PVFRIS 100 is effectively about zero (when full open) to total (when fully closed). The optional flow rate settings which may be indicated to the operator are therefore not just optional flow rate settings for the adjustable flow rate controller 110 itself, but rather are optional flow rate settings for the entire PVFRIS 100.

Figure 5:
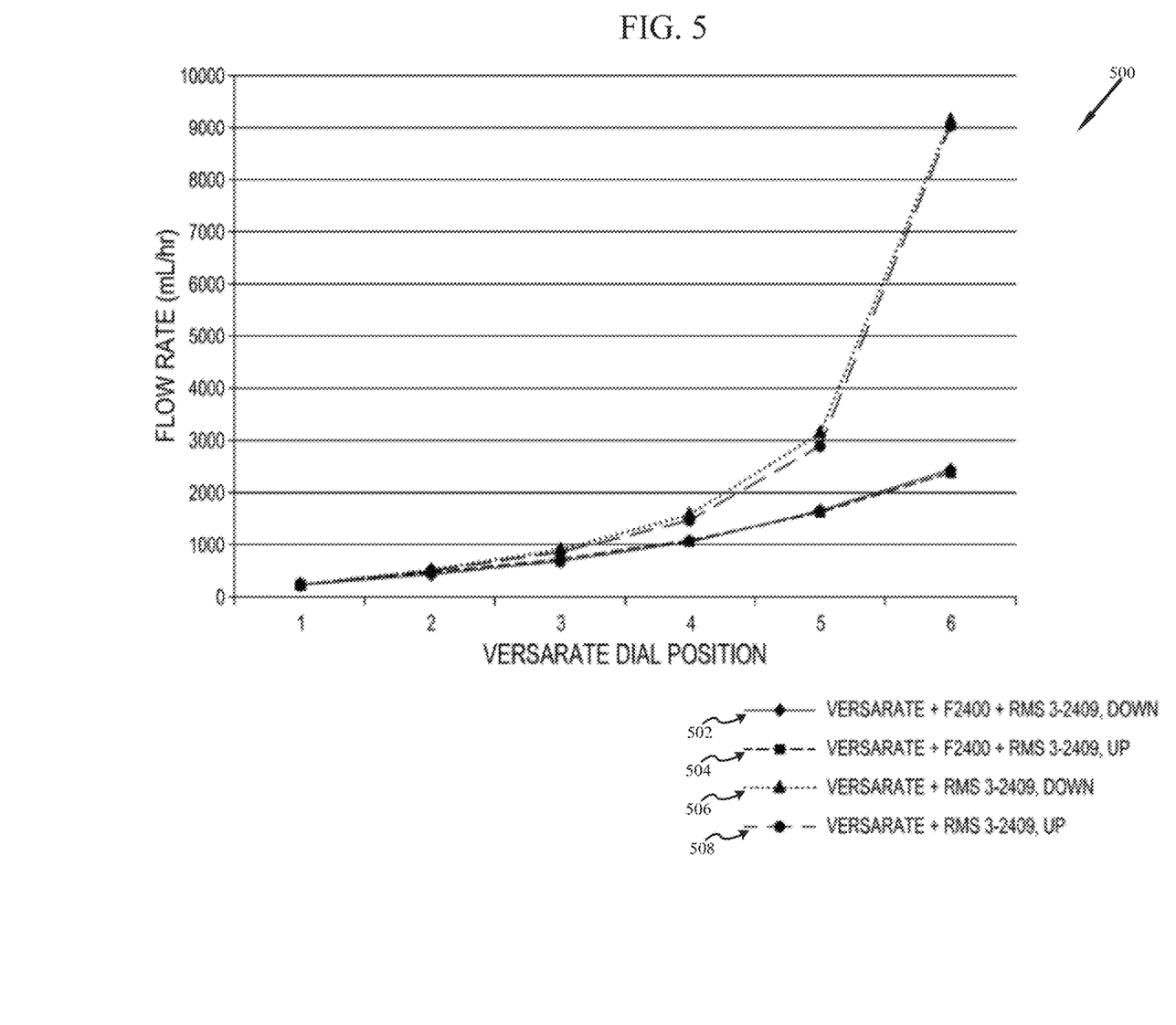
FIG. 5 is a table of performance data for a precision variable flow rate infusion system in accordance with at least one embodiment as compared to a typical infusion rate system.

FIG. 5 presents a chart of flow rate control for an embodiment of PVFRIS 100 as compared to a typical infusion system depending principally upon an adjustable controller. For both, the adjustable flow rate controller 110 is a commercially available Versarate® flow controller as provided to the market by EMID Technology Corporation. In addition, both testing graphs utilized a needle set identified as RMS 3-2409 as provided by RMS Medical Products. The key and advantageous difference being RMS Flow Control tubing identified as F2400 which provides 2400 ml/hour maximum flow rate. The data points shown in FIG. 5 were gathered in testing performed in the two directions of operation—which is to say turning DOWN the flow rate from highest to lowest dial setting position, and turning UP the flow rate from lowest to highest dial setting position.

As is shown by graph lines 502 and 504 representing the results from an embodiment of PVFRIS 100, the granularity of variable flow rate is very precise and consistent. The maximum flow rate is clearly 2400 ml, and there are no substantial jumps between the 5 indicated dial position options. In addition, the consistency of flow rate for any given dial position is substantially identical regardless of whether turning UP or DOWN.

As shown by graph lines 506 and 508 this is not the case for the non-PVFRIS 100 embodiment, shown to be the Versarate® flow controller and needle set alone. Indeed for both graph lines 506 and 508 there is a substantial jump between dial positions 4 and 5 and even a grater jump between dial positions 5 and 6. Further, there is apparent variability at both dial position 5 and 4 depending on whether turning UP or DOWN.

As different infusion liquids may well have different maximum dosage flow rates, different instances of PVFRIS 100 may be provided to accommodate desired infusions with a plurality of different liquids, yet each instance of PVFRIS 100 permits precision flow rate adjustment under each initial maximum dosage flow rate. As demonstrated by FIG. 5, the differences between possible position settings of the fluid pathway modifier 204 may be very slight. As such, calibration of each varying embodiment of PVFRIS 100 is typically performed so as to provide flow rate indications that are specifically established and reliable.

Figure 6:
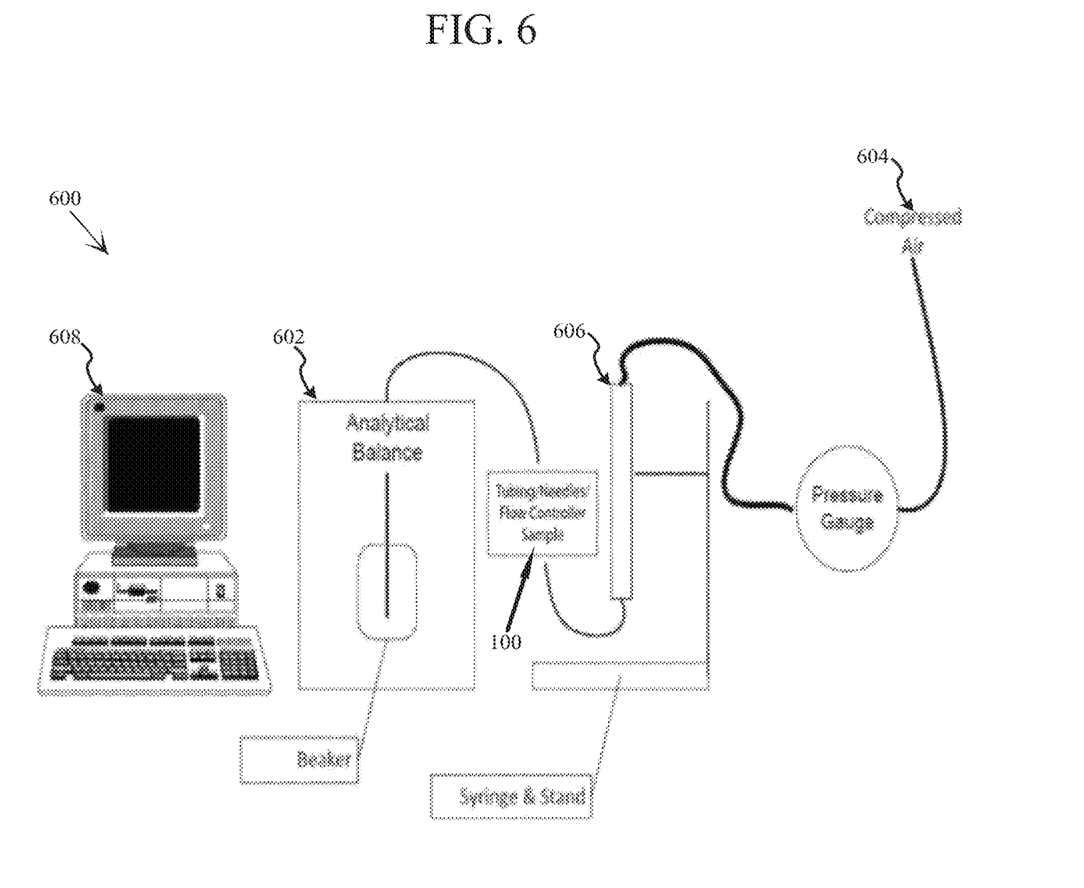
FIG. 6 is a conceptual illustration of a calibration system for a precision variable flow rate infusion system in accordance with at least one embodiment.

FIG. 6 presents an exemplary calibration system 600 as may be used in at least one embodiment to calibrate PVFRIS 100. More specifically, it has been found that a gravimetric system consisting of an analytical balance 602, a calibrated pressure source 604, a fluid reservoir 606, and of course fluids of known viscosity to be used in the testing procedure provide accurate and repeatable measures of consistent flow rates for tested embodiments of PVFRIS 100.

Typically, many infusion applications employ isotonic saline as the test fluid, however at the pressure of 0.9 bar and viscosity of the anticipated infusion medications, the use of isotonic saline will result in non-laminar flow and result in significant error. The use of fluids having higher viscosity and reduced pressure more appropriately parallels actual infusion conditions and permits accurate flow rate measurement and consequently calibration.

With respect to FIG. 6, the calibration system 600 may itself be calibrated by filling the fluid reservoir 606 with a fluid of a defined viscosity with a defined pressure and defined temperature (e.g., 21° C.). An embodiment of PVFRIS 100 is then disposed between the fluid reservoir 606 and the analytical balance, the outlet 114 of the PVFRIS 100 connected to a wide bore needle placed below the fluid line of an open beaker on the analytical balance 602. When pressure is applied to the fluid in the fluid reservoir 606, the analytical balance receives a time signal from the computer 608 to capture the mass at specific time intervals. Based on these recorded mass readings, and using the density of the fluid, the computer operates to convert the readings into fluid volume flow rate.

This process is repeated in turn for each optional setting of the adjustable flow rate controller 110, i.e., the fluid pathway modifier 204 such as the dial position. For at least one embodiment, ten recordings are made for each optional setting of the adjustable flow rate controller 110. This initializing process may also be performed for each direction, as in DOWN to UP and UP to DOWN so as to note any setting position discrepancy based on direction of setting modification.

It should be specifically noted that each adjustable flow rate controller 110 has an intended pre-defined flow direction as specified by the manufacturer. In light of the precise and low flow rates permitted by PVFRIS 100, it has been discovered through repeated testing that in some instances performance is enhanced by incorporating the adjustable flow rate controller 110 in PVFRIS 100 to provide a flow direction that is opposite to the pre-defined flow direction. More specifically, for some flow rates at specific pressures less leakage, and in fact no leakage, is obtained in PVFRIS 100 by reversing the orientation of adjustable flow rate controller 110.

As this initial calibration process operates with an actual liquid, PVFRIS 100 is potentially no longer sterile. However, having determined the precise liquid flow rate for a given setting on the adjustable flow rate controller 110, the calibration system 600 may be drained and dried. Now, a sterile gas is passed through PVFRIS 100 at the same setting on the adjustable flow rate controller 110. The flow rate of the gas will likely be different from the liquid, however, the flow rate of the gas may be used to calibrate other PVFRIS 100 devices. As such, one PVFRIS 100 may be used to establish the initial flow rate values for each optional setting of the adjustable flow rate controller 110, and sterile gas may then be used to certify a plurality of substantially similar embodiments of PVFRIS 100.

Figure 7:
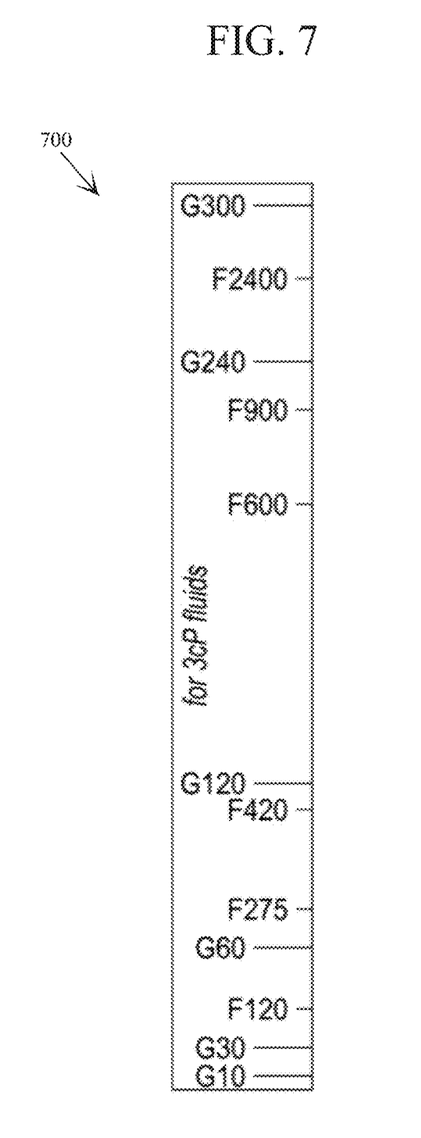
FIG. 7 is a conceptual illustration of a visual indicator strip provided for a precision variable flow rate infusion system in accordance with at least one embodiment.

Based on these calibrations, new visual guides may be provided, such as visual guide strip 700, shown in FIG. 7 to be affixed about adjustable flow rate controller 110 so as to provide the operator of PVFRIS 100 with a truly accurate and meaningful visual indicator directly on adjustable flow rate controller 110 that does not require cross reference of the selected position to a table identifying a potential plurality of different liquids. It is understood and appreciated that the visual indicator, i.e., visual guide strip 700 may take many forms—such as but not limited to a range of numbers corresponding to different flow rates, a tapering line indicating relative flow rate, a color spectrum indicating a change in flow rate, or other optional designation as may be appropriate for a given situation.

Having described embodiments of PVFRIS 100, other embodiments relating to at least one method 800 of using PVFRIS 100 will now be discussed with respect to FIG. 8. It will be appreciated that the described method need not be performed in the order in which it is herein described, but that this is merely exemplary of one method of using PVFRIS 100.

Figure 8:
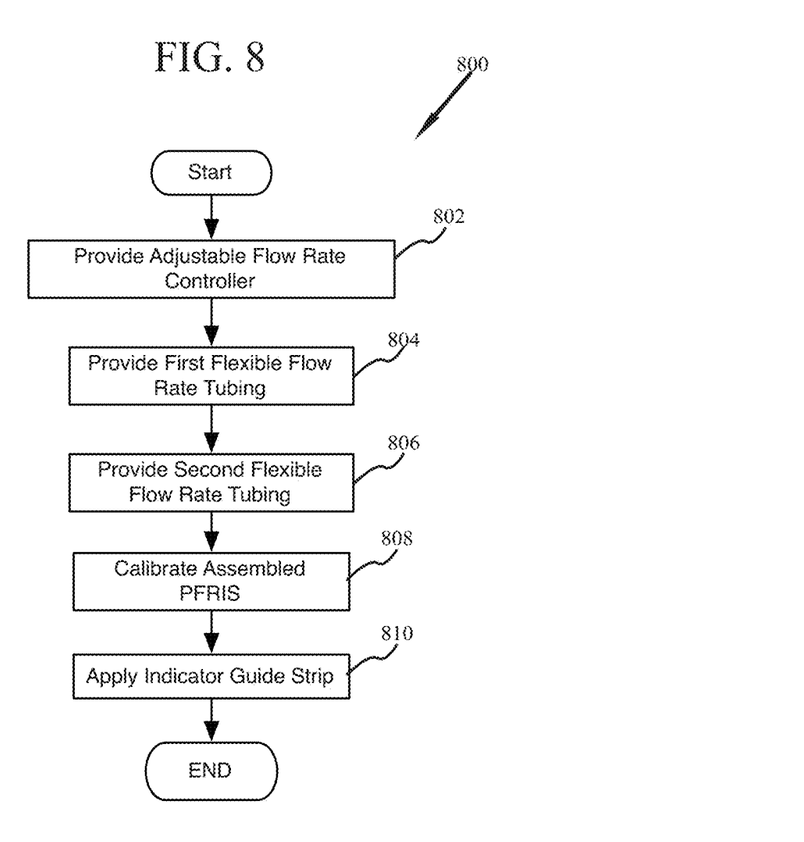
FIG. 8 is a high level flow diagram illustrating a method of providing a precision variable flow rate infusion system in accordance with at least one embodiment.

FIG. 8 conceptually illustrates a high level flow diagram depicting at least one method 800 for providing a precision variable flow rate infusion system as shown in FIGS. 1-4. Moreover, method 800 generally commences with providing an adjustable flow rate controller 110, block 802. The adjustable flow rate controller 110 has an inlet 200 and an outlet 202 and at least one internal fluid pathway there between and a fluid pathway modifier 204 structured and arranged to modify the internal fluid pathway from the inlet 200 to the outlet 202 from a closed pathway to a maximum pathway, with a plurality of different flow rate pathways there between.

Method 800 continues by providing a first flexible flow rate tubing 108, disposed between the reservoir 104 and the inlet of the adjustable flow rate controller 110, block 804. This first flexible flow rate tubing 108 has a first pre-defined flow rate.

Method 800 then continues by providing a second flexible flow rate tubing 120, disposed between the outlet 202 of the adjustable flow rate controller 110 and the patient 106, block 806. This second flexible flow rate tubing 120 has a second pre-defined flow rate.

As described above, for at least one embodiment, the first and second flexile flow rate tubing 108, 120 and the maximum adjuster flow rate of the adjustable flow rate controller 110 determine the maximum flow rate of the liquid 102 from the reservoir 104 to the patient and the adjustable flow rate controller 110 permits precision flow rate control from an off flow rate to about the maximum flow rate permitted by the first and the second flexile flow rate tubing 108, 120. More specifically, the first pre-defined flow rate and the second pre-defined flow rate cooperatively combine to be equal to or less than a maximum dosage flow rate for the liquid 102 from the reservoir 104, the first pre-defined flow rate and the second pre-defined flow rate being less than the initial potential outflow rate of the reservoir.

Method 800, further continues optionally by calibrating the assembled PVFRIS 100, block 808. With the calibration set for the optional settings of the adjustable flow rate controller 110, a visual guide strip 700 is affixed to the adjustable flow rate controller 110, block 810. As noted above, the visual guide strip 700 provides an operator of PVFRIS 100 with variable flow rate indicators for the entire PVFRIS 100, and not merely the adjustable flow rate controller 110.

Changes may be made in the above methods, systems and structures without departing from the scope hereof. It should thus be noted that the matter contained in the above description and/or shown in the accompanying drawings should be interpreted as illustrative and not in a limiting sense. Indeed many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A method for providing a precision variable flow rate infusion system for delivering a liquid driven by a constant pressure pump from a reservoir having an initial outflow rate to a patient at an adjustable flow rate equal to or less than a maximum dosage flow rate for the liquid, comprising:

providing an adjustable flow rate controller having an inlet and an outlet, at least one internal fluid pathway there between and a fluid pathway modifier structured and arranged to modify the at least one internal fluid pathway from the inlet to the outlet from a closed pathway providing a zero flow rate to a maximum flow pathway providing a maximum adjuster flow rate with a plurality of different flow rate pathways therebetween, a flow rate scale visually indicating variable flow rates from the maximum dosage flow rate of the liquid to the zero flow rate of the liquid;

providing a first flexible flow rate tubing having a length from a proximal end to a distal end and a first pre-defined flow rate generally established by a consistent internal diameter along the length to create a known flow rate for the liquid passing therethrough, the first flexible flow rate tubing disposed between the reservoir and the inlet of the adjustable flow rate controller;

providing a second flexible flow rate tubing having a second length from a second proximal end to a second distal end and a second pre-defined flow rate generally established by a consistent second internal diameter along the second length to create a second known flow rate for the liquid passing therethrough, the second flexible flow rate tubing disposed between the outlet of the adjustable flow rate controller and the patient, the first known flow rate and the second known flow rate combining to provide a third known flow rate not exceeding the maximum dosage flow rate for the liquid;

wherein the first pre-defined flow rate and the second pre-defined flow rate and the maximum adjuster flow rate cooperatively combine to be equal to or less than the maximum dosage flow rate for the liquid from the reservoir; and wherein the combination of the first pre-defined flow rate and the second pre-defined flow rate and the maximum adjuster flow rate determine a maximum delivery flow rate of the liquid from the reservoir through the system, and the adjustable flow rate controller permitting precision flow rate control from an off flow rate to about the maximum flow rate permitted by the combination of the first pre-defined flow rate, the second pre-defined flow rate and the maximum adjuster flow rate.

2. The method of claim 1, wherein the first pre-defined flow rate and the second pre-defined flow rate are selected to combine and provide the maximum dosage flow rate for the liquid from the reservoir, the maximum adjuster flow rate being an unrestrained flow rate that does not substantially affect the maximum dosage flow rate for the liquid as provided by the first pre-defined flow rate and the second pre-defined flow rate.

3. The method of claim 1, wherein the first pre-defined flow rate provided to the inlet of the adjustable flow rate controller by the first flexible flow rate tubing limits the adjustable flow rate controller to an adjustable range at or below the maximum dosage flow rate for the liquid.

4. The method of claim 1, wherein the fluid pathway modifier is provided by the inlet and the outlet rotating relative to each other to modify the at least one internal pathway from the inlet to the outlet from the closed pathway to the maximum flow pathway with a plurality of different flow rate pathways there between.

5. The method of claim 1, wherein the fluid pathway modifier is provided by a plurality of differently sized internal channels, a selector structured and arranged to select and deselect one or more of the differently sized internal channels to modify the internal pathway from the inlet to the outlet from the closed pathway to the maximum flow pathway with a plurality of different flow rate pathways there between.

6. The method of claim 1, wherein the adjustable flow rate controller has a pre-defined flow direction, the adjustable flow rate controller disposed between the first flexible flow rate tubing and the second flexible flow rate tubing to provide a flow direction through the adjustable flow rate controller opposite to the pre-defined flow direction.

7. The method of claim 1, further including pre-calibrating the adjustable flow rate controller with sterile gas correlated to an intended liquid to provide a flow rate scale tuned for each assembly of the first flexible flow rate tubing, the second flexible flow rate tubing and the adjustable flow rate controller.

8. The method of claim 1, wherein the first pre-defined flow rate of the first flexible flow rate tubing is equal to or greater than the second pre-defined flow rate of the second flexible flow rate tubing.

9. The method of claim 1, wherein the second pre-defined flow rate of the second flexible flow rate tubing is equal to or greater than the first pre-defined flow rate of the first flexible flow rate tubing.

10. The method of claim 1, wherein the first pre-determined flow rate of the first flexible flow rate tubing is selected from the group consisting of: about 30 mL/hr, about 45 mL/hr, about 60 mL/hr, about 120 mL/hr, about 180 mL/hr, about 420 mL/hr, about 600 mL/hr, about 900 mL/hr, about 1200 mL/hr, and about 2400 mL/hr.

11. The method of claim 1, wherein the second pre-determined flow rate of the second flexible flow rate tubing is selected from the group consisting of: about 30 mL/hr, about 45 mL/hr, about 60 mL/hr, about 120 mL/hr, about 180 mL/hr, about 420 mL/hr, about 600 mL/hr, about 900 mL/hr, about 1200 mL/hr, and about 2400 mL/hr.

12. A method for providing a precision variable flow rate infusion system for delivering a liquid driven by a constant pressure pump from a reservoir having an initial outflow rate to a patient at an adjustable flow rate equal to or less than a maximum dosage flow rate for the liquid, comprising:
    providing a first flexible flow rate tubing having a length from a proximal end to a distal end and a pre-defined flow rate generally established by a consistent internal diameter along the length to create a known flow rate for the liquid passing therethrough, the known flow rate not exceeding the maximum dosage flow rate for the liquid; and
    providing an adjustable flow rate controller having an inlet and an outlet, at least one internal fluid pathway there between and a fluid pathway modifier structured and arranged to modify the at least one internal fluid pathway from the inlet to the outlet from a closed pathway providing a zero flow rate to a maximum flow pathway providing a maximum adjuster flow rate with a plurality of different flow rate pathways therebetween, a flow rate scale visually indicating variable flow rates from the maximum dosage flow rate of the liquid to the zero flow rate of the liquid, the adjustable flow rate controller inlet coupled to the first flexible flow rate tubing to receive the liquid at the known flow rate established by the first flexible flow rate tubing;
    wherein the pre-defined flow rate and the maximum adjuster flow rate cooperatively combining to be equal to or less than the maximum dosage flow rate for the liquid from the reservoir;
    wherein the combination of the pre-defined flow rate and the maximum adjuster flow rate determine a maximum delivery flow rate of the liquid from the reservoir through the system, and the adjustable flow rate controller permitting precision flow rate control from an off flow rate to about the maximum delivery flow rate permitted by the combination of the pre-defined flow rate and the maximum adjuster flow rate.

13. The method of claim 12, wherein the variable flow rate infusion system is pre-calibrated with sterile gas correlated to an intended liquid to provide the flow rate scale tuned for each assembly of the first flexible flow rate tubing and adjustable flow rate controller.

14. The method of claim 12, wherein the pre-defined flow rate of the first flexible flow rate tubing is selected at the maximum dosage flow rate for the liquid from the reservoir, the maximum adjuster flow rate being an unrestrained flow rate that does not substantially affect the maximum dosage flow rate for the liquid as provided by the first flexible flow rate tubing.

15. The method of claim 12, wherein the known flow rate provided to the inlet of the adjustable flow rate controller by the first flexible flow rate tubing limits the adjustable flow rate controller to an adjustable range at or below the maximum dosage flow rate.

16. The method of claim 12, wherein the fluid pathway modifier is provided by the inlet and the outlet rotating relative to each other to modify the at least one internal pathway from the inlet to the outlet from a closed pathway to a maximum flow pathway with a plurality of different flow rate pathways there between.

17. The method of claim 12, wherein the fluid pathway modifier is provided by a plurality of differently sized internal channels, a selector structured and arranged to select and deselect one or more of the differently sized internal channels to modify the internal pathway from the inlet to the outlet from the closed pathway to the maximum flow pathway with a plurality of different flow rate pathways there between.

18. The method of claim 12, wherein the adjustable flow rate controller has a pre-defined flow direction, the adjustable flow rate controller incorporated to provide a flow direction opposite to the pre-defined flow direction.

19. The method of claim 12, wherein the adjustable flow rate controller is pre-calibrated with sterile gas correlated to an intended liquid to provide a flow rate scale tuned for each assembly of the first flexible flow rate tubing and adjustable flow rate controller.

20. The method of claim 12, wherein the adjustable flow rate controller is disposed along the first flexible flow rate tubing between the reservoir and the patient.

21. The method of claim 12, further including a second flexible tubing, the first flexible flow rate tubing disposed between the reservoir and the inlet of the adjustable flow rate controller and the second flexible tubing disposed between the outlet of the adjustable flow rate controller and the patient.

22. The method of claim 21, wherein the second flexible tubing is a second flexible flow rate tubing having a pre-defined flow rate equal to or less than the pre-defined flow rate of the first flexible flow rate tubing.

23. The method of claim 12, wherein the pre-determined flow rate of the first flexible flow rate tubing is selected from the group consisting of: about 30 mL/hr, about 45 mL/hr, about 60 mL/hr, about 120 mL/hr, about 180 mL/hr, about 420 mL/hr, about 600 mL/hr, about 900 mL/hr, about 1200 mL/hr, and about 2400 mL/hr.

\* \* \* \* \*